(12) United States Patent  (10) Patent No.: US 9,243,987 B2
Chanda et al.  (45) Date of Patent: Jan. 26, 2016

(54) METHOD OF DETERMINING FABRIC TYPE OF A LAUNDRY LOAD IN A LAUNDRY TREATING APPLIANCE

(71) Applicant: Whirlpool Corporation, Benton Harbor, MI (US)

(72) Inventors: Hirak Chanda, Troy, MI (US); Kaustav Ghosh, Benton Harbor, MI (US); Andrew J. Leitert, Eau Claire, MI (US); Karl David McAllister, Stevensville, MI (US); Amy L. Rapson, Holland, MI (US); Jon D. Strait, Saint Joseph, MI (US); Yingqin Yuan, Saint Joseph, MI (US)

(73) Assignee: Whirlpool Corporation, Benton Harbor, MI (US)

( * ) Notice: Subject to any disclaimer, the term of this patent is extended or adjusted under 35 U.S.C. 154(b) by 455 days.

(21) Appl. No.: 13/874,517

(22) Filed: May 1, 2013

(65) Prior Publication Data

US 2014/0326067 A1  Nov. 6, 2014

(51) Int. Cl.
*G01N 9/00* (2006.01)
*G01N 9/30* (2006.01)
*D06F 39/00* (2006.01)

(52) U.S. Cl.
CPC ............... *G01N 9/00* (2013.01); *D06F 39/003* (2013.01); *G01N 9/30* (2013.01)

(58) Field of Classification Search
USPC ........................................................ 73/32 R
See application file for complete search history.

(56) References Cited

U.S. PATENT DOCUMENTS

| | | | |
|---|---|---|---|
| 4,400,838 A | 8/1983 | Steers et al. | |
| 5,144,819 A | 9/1992 | Hiyama et al. | |
| 5,161,393 A | 11/1992 | Payne et al. | |
| 5,230,228 A | 7/1993 | Nakano et al. | |
| 5,259,217 A | 11/1993 | Civanelli et al. | |
| 5,768,729 A | 6/1998 | Cracraft | |
| 5,897,672 A | 4/1999 | Badami et al. | |
| 6,023,950 A | 2/2000 | Battistella | |
| 6,784,997 B2 | 8/2004 | Lorenz et al. | |
| 7,421,752 B2 | 9/2008 | Donadon et al. | |
| 7,735,239 B2 | 6/2010 | Jeong et al. | |
| 8,196,441 B2 | 6/2012 | Hendrickson et al. | |
| 2004/0118008 A1 | 6/2004 | Jeong et al. | |
| 2009/0307850 A1 | 12/2009 | Czyzewski et al. | |
| 2010/0000024 A1 | 1/2010 | Hendrickson et al. | |
| 2010/0000264 A1 | 1/2010 | Luckman et al. | |
| 2010/0000573 A1 | 1/2010 | Hendrickson et al. | |
| 2010/0000581 A1 | 1/2010 | Doyle et al. | |

(Continued)

FOREIGN PATENT DOCUMENTS

AT  84332 T  1/1993
DE  102010000428 A1  10/2010

(Continued)

OTHER PUBLICATIONS

German Search Report for Counterpart DE102014104635.8, dated Oct. 30, 2014.

*Primary Examiner* — John Fitzgerald
*Assistant Examiner* — David Z Huang

(57) ABSTRACT

A method of determining a fabric type for a laundry load can include comparing the density of the laundry load in a first wetted state, which may be a dry state or a partially saturated state, to the density of the laundry load in a second wetted state, which may be a partially saturated, fully saturated, or beyond fully saturated state, and determining a fabric type based on the comparison.

20 Claims, 7 Drawing Sheets

(56) References Cited

U.S. PATENT DOCUMENTS

| | | |
|---|---|---|
| 2010/0000586 A1 | 1/2010 | Hendrickson |
| 2010/0024490 A1 | 2/2010 | Nieh et al. |
| 2010/0064445 A1 | 3/2010 | Nieh et al. |
| 2010/0205825 A1 | 8/2010 | Ashrafzadeh et al. |
| 2011/0030150 A1 | 2/2011 | Ashrafzadeh et al. |
| 2011/0030239 A1 | 2/2011 | Dey et al. |
| 2011/0146102 A1 | 6/2011 | Bellinetto et al. |
| 2012/0118022 A1* | 5/2012 | Ashrafzadeh ......... D06F 39/003 68/12.04 |
| 2012/0266389 A1 | 10/2012 | Ihne et al. |
| 2012/0298427 A1 | 11/2012 | Bringewatt et al. |
| 2013/0185872 A1* | 7/2013 | Chanda ................. D06F 13/06 8/137 |

FOREIGN PATENT DOCUMENTS

| | | |
|---|---|---|
| DE | 102010016875 A1 | 2/2011 |
| DE | 102011109014 A1 | 11/2012 |
| EP | 0159202 A1 | 10/1985 |
| EP | 0649932 A1 | 4/1995 |
| EP | 0649933 A1 | 4/1995 |
| EP | 0787848 A1 | 8/1997 |
| EP | 1295979 A2 | 3/2003 |
| EP | 1844191 B1 | 3/2010 |
| FR | 2894996 A1 | 6/2007 |
| KR | 19980018355 A | 12/1999 |
| KR | 20050050260 A | 5/2005 |
| WO | 2011080231 A2 | 7/2011 |

* cited by examiner

| Dry Density \ Wetted Density | Low | Medium | High |
|---|---|---|---|
| Low | Synthetic | Bulky Items | |
| Medium | | Casual/Synthetic Cotton Blends | Terry |
| High | Lingerie | Denim | |

FIG. 5

| Wetted Density / Dry Density | Low | Medium | High |
|---|---|---|---|
| Low | Absorbency – Low<br>Bending – Low<br>Elasticity - Medium | Absorbency – High<br>Bending – Medium<br>Elasticity - High | |
| Medium | | Absorbency – Medium<br>Bending – Low<br>Elasticity - Medium | Absorbency – High<br>Bending – Low<br>Elasticity - Medium |
| High | | Absorbency – Medium<br>Bending – Medium<br>Elasticity - Medium | |

FIG. 6

METHOD OF DETERMINING FABRIC TYPE OF A LAUNDRY LOAD IN A LAUNDRY TREATING APPLIANCE

BACKGROUND

Parameters for an operation cycle of a laundry treating appliance can depend on several factors, such as the size of a laundry load and the type of fabric of the laundry load. In some laundry treating appliances, the user manually inputs a fabric type through a user interface. However, it may be desirable to have the appliance automatically determine the fabric type because, for example, manual input may be perceived as inconvenient to the user and may result in a subjective, inaccurate characterization of the laundry type.

SUMMARY

A method of determining a fabric type for a laundry load according to one embodiment of the invention includes determining a density of the laundry load in a first wetted state to define a first density, determining a density of the laundry load in a second wetted state to define a second density, comparing the first density and the second density, and determining a fabric type based on the comparison.

BRIEF DESCRIPTION OF THE DRAWINGS

In the drawings:

FIG. 5 is an exemplary reference table that can be employed with the method in the flowchart of FIG. 3.

FIG. 6 is another embodiment of an exemplary reference table that can be employed with the method in the flowchart of FIG. 3.

DESCRIPTION OF EMBODIMENTS OF THE INVENTION

Figure 1:
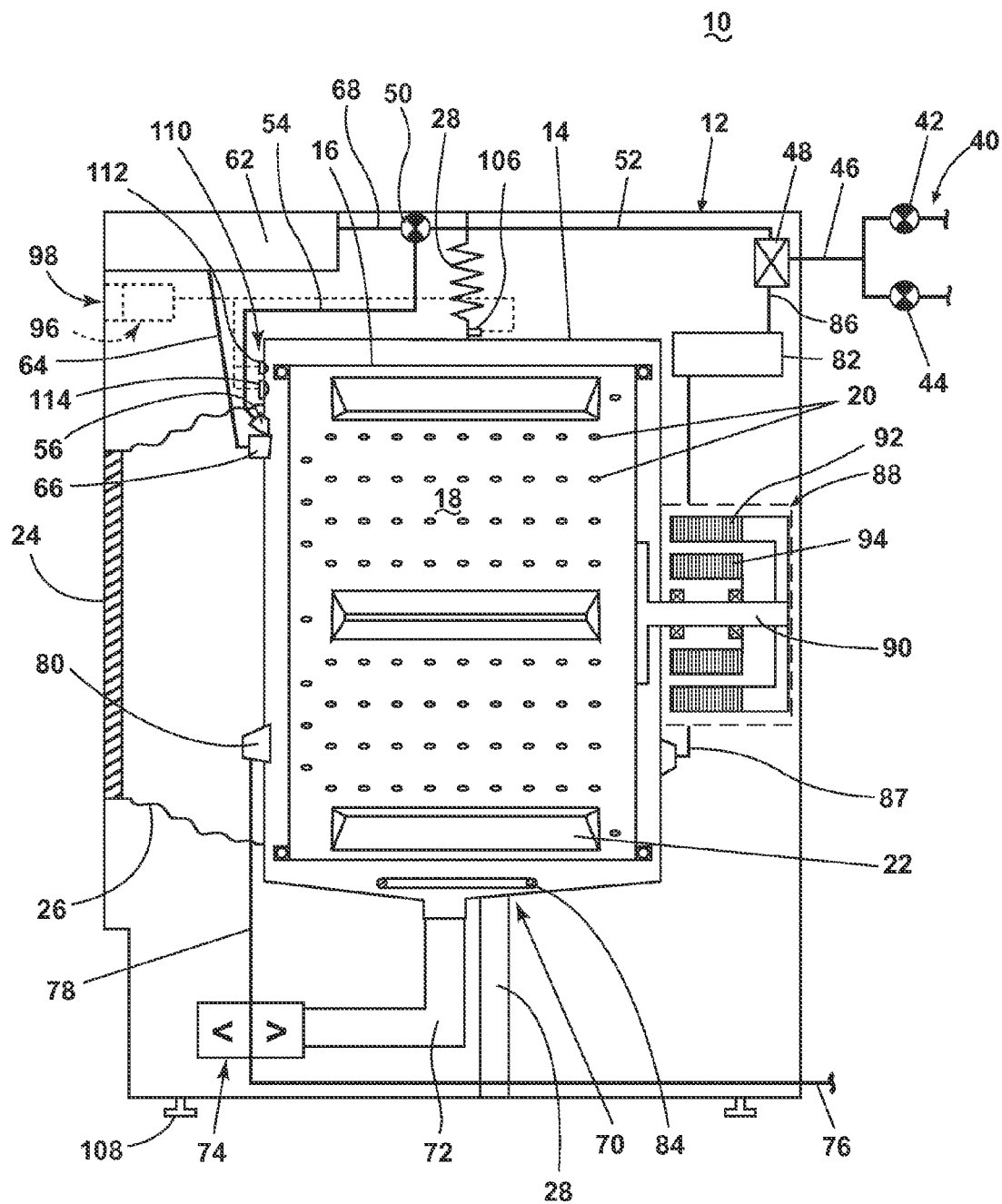
FIG. 1 is a schematic view of a laundry treating appliance in the form of a washing machine according to an embodiment of the invention.

FIG. 1 is a schematic view of a laundry treating appliance according to an embodiment of the invention. The laundry treating appliance may be any appliance that performs a cycle of operation to clean or otherwise treat items placed therein, non-limiting examples of which include a horizontal or vertical axis clothes washer, a combination washing machine and dryer, a tumbling or stationary refreshing/revitalizing machine, an extractor, a non-aqueous washing apparatus, and a revitalizing machine.

The laundry treating appliance of FIG. 1 is illustrated as a washing machine 10, which may include a structural support system comprising a cabinet 12 that defines a housing within which a laundry holding system resides. The cabinet 12 may be a housing having a chassis and/or a frame, defining an interior enclosing components typically found in a conventional washing machine, such as motors, pumps, fluid lines, controls, sensors, transducers, and the like. Such components will not be described further herein except as necessary for a complete understanding of the invention.

The laundry holding system comprises a tub 14 supported within the cabinet 12 by a suitable suspension system and a drum 16 provided within the tub 14 and defining at least a portion of a laundry treating chamber 18. The drum 16 may include a plurality of perforations 20 such that liquid may flow between the tub 14 and the drum 16 through the perforations 20. A plurality of baffles 22 may be disposed on an inner surface of the drum 16 to lift the laundry load received in the treating chamber 18 while the drum 16 rotates. It is also within the scope of the invention for the laundry holding system to comprise only a tub with the tub defining the laundry treating chamber.

The laundry holding system may further include a door 24 that may be movably mounted to the cabinet 12 to selectively close both the tub 14 and the drum 16. A bellows 26 may couple an open face of the tub 14 with the cabinet 12, with the door 24 sealing against the bellows 26 when the door 24 closes the tub 14.

The washing machine 10 may further include a suspension system 28 for dynamically suspending the laundry holding system within the structural support system.

The washing machine 10 may further include a liquid supply system for supplying water to the washing machine 10 for use in treating laundry during a cycle of operation. The liquid supply system may include a source of water, such as a household water supply 40, which may include separate valves 42 and 44 for controlling the flow of hot and cold water, respectively. Water may be supplied through an inlet conduit 46 directly to the tub 14 by controlling first and second diverter mechanisms 48 and 50, respectively. Each of the diverter mechanisms 48, 50 may be a diverter valve having two outlets such that the diverter mechanisms 48, 50 may selectively direct a flow of liquid to one or both of two flow paths. Water from the household water supply 40 may flow through the inlet conduit 46 to the first diverter mechanism 48 that may direct the flow of liquid to a supply conduit 52. The second diverter mechanism 50 on the supply conduit 52 may direct the flow of liquid to a tub outlet conduit 54 that may be provided with a spray nozzle 56 configured to spray the flow of liquid into the tub 14. In this manner, water from the household water supply 40 may be supplied directly to the tub 14.

The washing machine 10 may also be provided with a dispensing system for dispensing treating chemistry to the treating chamber 18 for use in treating the laundry according to a cycle of operation. The dispensing system may include a dispenser 62, which may be a single use dispenser, a bulk dispenser, or a combination of a single and bulk dispenser. Non-limiting examples of suitable dispensers are disclosed in U.S. Pat. No. 8,196,441 to Hendrickson et al., issued Jun. 12, 2012, entitled "Household Cleaning Appliance with a Dispensing System Operable Between a Single Use Dispensing System and a Bulk Dispensing System," U.S. Pub. No. 2010/0000024 to Hendrickson et al., filed Jul. 1, 2008, entitled "Apparatus and Method for Controlling Laundering Cycle by Sensing Wash Aid Concentration," U.S. Pub. No. 2010/0000573 to Hendrickson et al., filed Jul. 1, 2008, entitled "Apparatus and Method for Controlling Concentration of Wash Aid in Wash Liquid," U.S. Pub. No. 2010/0000581 to Doyle et al., filed Jul. 1, 2008, entitled "Water Flow Paths in a Household Cleaning Appliance with Single Use and Bulk Dispensing," U.S. Pub. No. 2010/0000264 to Luckman et al., filed Jul. 1, 2008, entitled "Method for Converting a Household Cleaning Appliance with a Non-Bulk Dispensing System to a Household Cleaning Appliance with a Bulk Dispensing System," U.S. Pub. No. 2010/0000586 to Hendrickson, filed Jun. 23, 2009, entitled "Household Cleaning Appliance with a Single Water Flow Path for Both Non-Bulk and Bulk Dispensing," and application Ser. No. 13/093,132, filed Apr. 25, 2011, entitled "Method and Apparatus for Dispensing Treating Chemistry in a Laundry Treating Appliance," which are herein incorporated by reference in full.

Regardless of the type of dispenser used, the dispenser 62 may be configured to dispense a treating chemistry directly to the tub 14 or mixed with water from the liquid supply system through a dispensing outlet conduit 64. The dispensing outlet conduit 64 may include a dispensing nozzle 66 configured to dispense the treating chemistry into the tub 14 in a desired pattern and under a desired amount of pressure. For example, the dispensing nozzle 66 may be configured to dispense a flow or stream of treating chemistry into the tub 14 by gravity, i.e., a non-pressurized stream. Water may be supplied to the dispenser 62 from the supply conduit 52 by directing the diverter mechanism 50 to direct the flow of water to a dispensing supply conduit 68.

Non-limiting examples of treating chemistries that may be dispensed by the dispensing system during a cycle of operation include one or more of the following: water, enzymes, fragrances, stiffness/sizing agents, wrinkle releasers/reducers, softeners, antistatic or electrostatic agents, stain repellents, water repellents, energy reduction/extraction aids, antibacterial agents, medicinal agents, vitamins, moisturizers, shrinkage inhibitors, color fidelity agents, and combinations thereof.

The washing machine 10 may also include a recirculation and drain system for recirculating liquid within the laundry holding system and draining liquid from the washing machine 10. Liquid supplied to the tub 14 through tub outlet conduit 54 and/or the dispensing supply conduit 68 typically enters a space between the tub 14 and the drum 16 and may flow by gravity to a sump 70 formed in part by a lower portion of the tub 14. The sump 70 may also be formed by a sump conduit 72 that may fluidly couple the lower portion of the tub 14 to a pump 74. The pump 74 may direct liquid to a drain conduit 76, which may drain the liquid from the washing machine 10, or to a recirculation conduit 78, which may terminate at a recirculation inlet 80. The recirculation inlet 80 may direct the liquid from the recirculation conduit 78 into the drum 16. The recirculation inlet 80 may introduce the liquid into the drum 16 in any suitable manner, such as by spraying, dripping, or providing a steady flow of liquid. In this manner, liquid provided to the tub 14, with or without treating chemistry, may be recirculated into the treating chamber 18 for treating the laundry therein.

The liquid supply and/or recirculation and drain system may be provided with a heating system that may include one or more devices for heating laundry and/or liquid supplied to the tub 14, such as a steam generator 82 and/or a sump heater 84. Liquid from the household water supply 40 may be provided to the steam generator 82 through the inlet conduit 46 by controlling the first diverter mechanism 48 to direct the flow of liquid to a steam supply conduit 86. Steam generated by the steam generator 82 may be supplied to the tub 14 through a steam outlet conduit 87. The steam generator 82 may be any suitable type of steam generator such as a flow through/in-line steam generator or a tank-type steam generator. Alternatively, the sump heater 84 may be used to generate steam in place of or in addition to the steam generator 82. In addition or alternatively to generating steam, the steam generator 82 and/or sump heater 84 may be used to heat the laundry and/or liquid within the tub 14 as part of a cycle of operation.

Additionally, the liquid supply and recirculation and drain system may differ from the configuration shown in FIG. 1, such as by inclusion of other valves, conduits, treating chemistry dispensers, sensors, such as water level sensors and temperature sensors, and the like, to control the flow of liquid through the washing machine 10 and for the introduction of more than one type of treating chemistry.

The washing machine 10 also includes a drive system for rotating the drum 16 within the tub 14. The drive system may include a motor 88, which may be directly coupled with the drum 16 through a drive shaft 90 to rotate the drum 16 about a rotational axis during a cycle of operation. The motor 88 may be a brushless permanent magnet (BPM) motor having a stator 92 and a rotor 94. Alternately, the motor 88 may be coupled to the drum 16 through a belt and a drive shaft to rotate the drum 16, as is known in the art. Other motors, such as an induction motor or a permanent split capacitor (PSC) motor, may also be used. The motor 88 may rotate the drum 16 at various speeds in either rotational direction.

The washing machine 10 also includes a control system for controlling the operation of the washing machine 10 to implement one or more cycles of operation. The control system may include a controller 96 located within the cabinet 12 and a user interface 98 that is operably coupled with the controller 96. The user interface 98 may include one or more knobs, dials, switches, displays, touch screens, and the like for communicating with the user, such as to receive input and provide output. The user may enter different types of information including, without limitation, cycle selection and cycle parameters, such as cycle options.

The controller 96 may include the machine controller and any additional controllers provided for controlling any of the components of the washing machine 10. For example, the controller 96 may include the machine controller and a motor controller. Many known types of controllers may be used for the controller 96. The specific type of controller is not germane to the invention. It is contemplated that the controller is a microprocessor-based controller that implements control software and sends/receives one or more electrical signals to/from each of the various working components to effect the control software. As an example, proportional control (P), proportional integral control (PI), and proportional derivative control (PD), or a combination thereof, a proportional integral derivative control (PID), may be used to control the various components.

Figure 2:
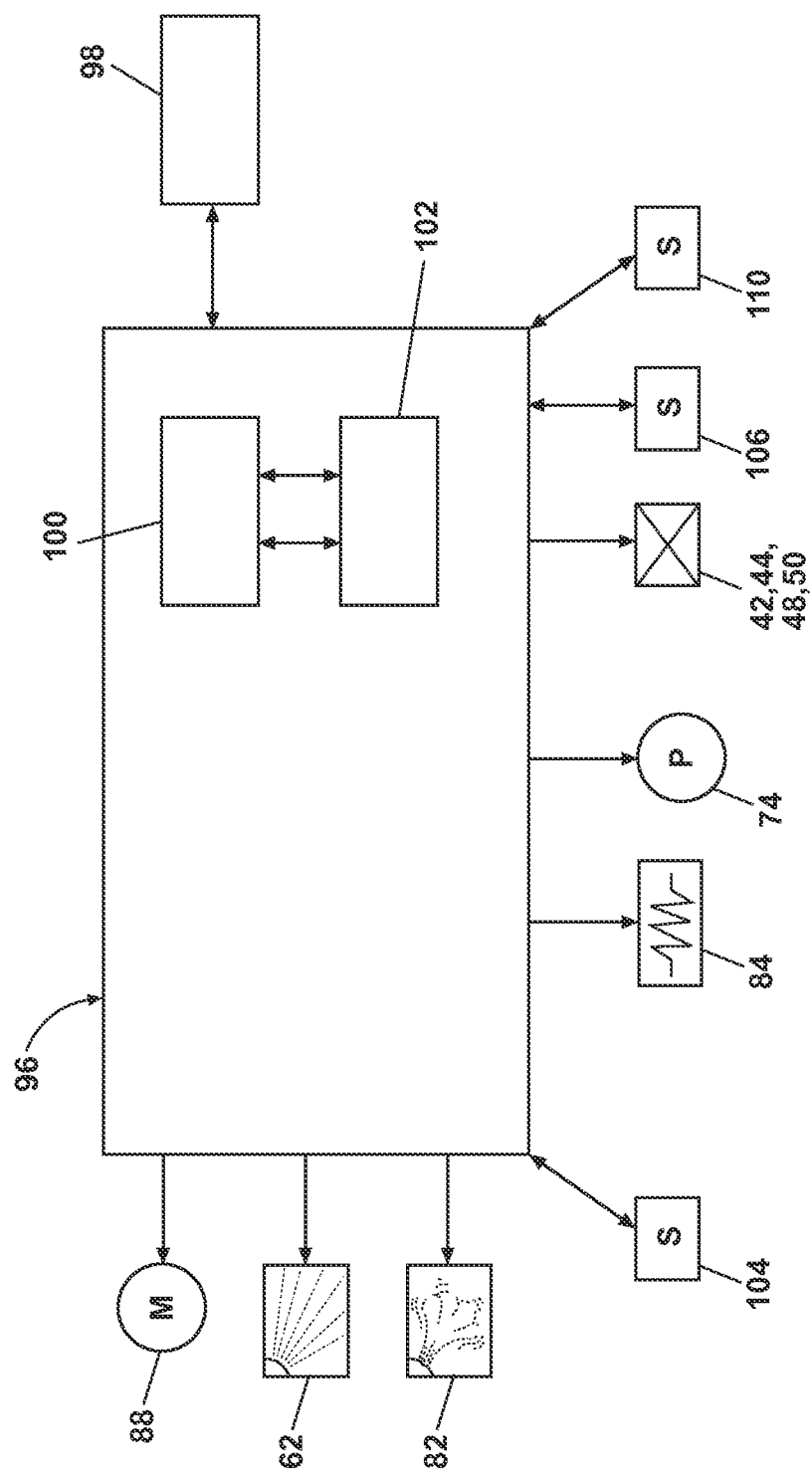
FIG. 2 is a schematic of a control system of the laundry treating appliance of FIG. 1 according to an embodiment of the invention.

As illustrated in FIG. 2, the controller 96 may be provided with a memory 100 and a central processing unit (CPU) 102. The memory 100 may be used for storing the control software that is executed by the CPU 102 in completing a cycle of operation using the washing machine 10 and any additional software. Examples, without limitation, of cycles of operation include: wash, heavy duty wash, bulky items wash, delicate wash, whites wash, quick wash, pre-wash, refresh, rinse only, and timed wash. The memory 100 may also be used to store information, such as a database or table, and to store data received from one or more components of the washing machine 10 that may be communicably coupled with the controller 96. The database or table may be used to store the various operating parameters for the one or more cycles of operation, including factory default values for the operating parameters and any adjustments to them by the control system or by user input.

The controller 96 may be operably coupled with one or more components of the washing machine 10 for communicating with and controlling the operation of the component to complete a cycle of operation. For example, the controller 96 may be operably coupled with the motor 88, the pump 74, the dispenser 62, the steam generator 82 and the sump heater 84 to control the operation of these and other components to implement one or more of the cycles of operation.

The controller 96 may also be coupled with one or more sensors 104 provided in one or more of the systems of the washing machine 10 to receive input from the sensors, which are known in the art and not shown for simplicity. Non-limiting examples of sensors 104 that may be communicably coupled with the controller 96 include: a treating chamber temperature sensor, a moisture sensor, a chemical sensor, a position sensor, and a motor torque sensor, which may be used to determine a variety of system and laundry characteristics, such as laundry load inertia or mass.

One or more load mass sensors 106 may also be included in the washing machine 10 in communication with the controller 96 and may be positioned in any suitable location for detecting the mass of laundry within the treating chamber 18. The one or more load mass sensors 106 may be any suitable type of sensor capable of measuring the mass of the laundry in the treating chamber 18. Non-limiting examples of load mass sensors 106 for measuring the mass of the laundry may include force transducers, such as, for example, load cells and strain gauges. It has been contemplated that the one or more of the load mass sensors 106 may be operably coupled to the suspension system 28 to sense the weight borne by the suspension system 28. The weight borne by the suspension system 28 correlates to the weight of the laundry loaded into the treating chamber 18 such that the sensor 106 may indicate the mass of the laundry loaded in the treating chamber 18.

Alternatively, it has been contemplated that the washing machine 10 may have one or more pairs of feet 108 extending from the cabinet 12 and supporting the cabinet 12 on the floor and that a weight sensor (not shown) may be operably coupled to at least one of the feet 108 to sense the weight borne by that foot 108, which correlates to the mass of the laundry loaded into the treating chamber 18. In another example, the amount of laundry within the treating chamber 18 may be determined based on motor sensor output, such as output from a motor torque sensor. The motor torque is a function of the inertia of the rotating drum and laundry. There are many known methods for determining the load inertia, and thus the load mass, based on the motor torque. As one example, the inertia may be determined by measuring the torque required to accelerate the laundry load at a constant rate. Alternatively, the mass of the laundry load can be determined from a measurement of the natural frequency of the drum 16 and the laundry load. Several methods are known for measuring the natural frequency, including exciting the laundry load with an impulse from a solenoid or other device and monitoring the frequency response with a receiver, such as an accelerometer or microphone. In a vertical axis washing machine, the natural frequency can be determined by exciting the laundry load with an impeller plate and monitoring the motor torque output. In yet another example, the mass can be determined by measuring the displacement of the tub 14 and/or the drum 16 resulting from the laundry load. The displacement can be measured in any suitable manner, including, without limitation, optical sensors, sonar devices, and linear variable differential transformers (LVDT).

It will be understood that the details of the load mass sensors are not germane to the embodiments of the invention and that any suitable method and sensors may be used to determine the mass of the laundry.

The washing machine 10 may also include one or more load volume sensors 110 in communication with the controller 96 for detecting the volume of the laundry load within the treating chamber 18. In one embodiment, the load volume sensor 110 may be in the form of an imaging device 112 to image the treating chamber 18 and/or the laundry load within the treating chamber 18. Examples of the imaging device 112 may include an optical sensor capable of capturing still or moving images, such as a camera. The images may be two-dimensional or three-dimensional. One suitable type of camera is a CMOS camera. Other exemplary imaging devices include a CCD camera, a digital camera, a video camera or any other type of device capable of capturing an image. The imaging device 112 may be located in any suitable position to view the treating chamber 18, and the particular location of the imaging device 112 may depend on the particular structure of the washing machine 10 and the desired position for obtaining an image.

The load volume sensor 110 may also have an illumination source 114 to aid the imaging device 112. The type of the illumination source 114 may vary. In one configuration, the illumination source 114 may be a typical incandescent washer light that is commonly used to illuminate the treating chamber 18. Alternatively, one or more LED lights may be used in place of an incandescent bulb. The illumination source 114 may also be located in any suitable position to aid in obtaining a desired image. Image analysis may be used to isolate the laundry load from other structures in the image, such as the drum 16, and determine the volume of the laundry load. Any suitable analytical technique may be employed to determine the volume of the laundry load from the images.

Alternative sensors and methods for determining the volume of the laundry load include, but are not limited to, optical or infrared sensing, such as measuring the reflectance of an optical laser; acoustic sensing, such as sonar and ultrasonic methods; measuring capacitance or inductance; employing the motor torque signal, and detecting the harmonic frequency of the drum 16 by striking the drum 16 and monitoring the frequency response with a receiver, such as an accelerometer or microphone.

It will be understood that the details of the load volume sensors are not germane to the embodiments of the invention and that any suitable method and sensors may be used to determine the volume of the laundry.

The previously described washing machine 10 provides an example of a laundry treating appliance that may be used to implement one or more embodiments of the invention. The embodiments of the method of the invention may be used to automatically determine a fabric type of the laundry load in the treating chamber 18 and set process parameters for a cycle of operation based on the determined fabric type.

Figure 3:
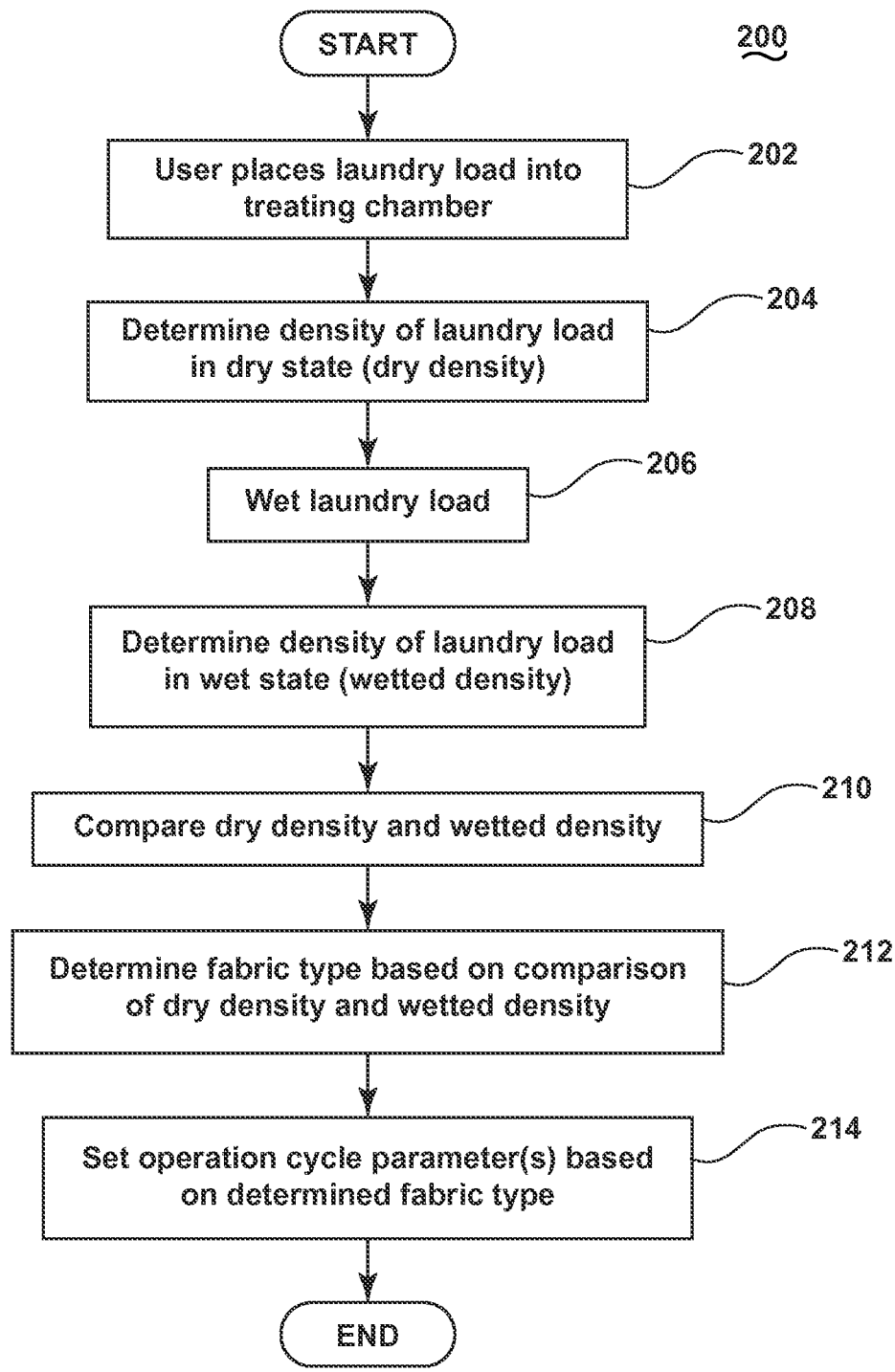
FIG. 3 is a flowchart of an embodiment of a method of determining fabric type based on dry and wetted densities of the laundry load.

FIG. 3 illustrates a flow chart of an embodiment of a method 200 for determining the fabric type of the laundry load in the washing machine 10 is illustrated. The sequence of steps depicted and described below for this method are for illustrative purposes only, and is not meant to be limiting as it is understood that the steps may proceed in a different logical order and that additional or intervening steps may be included without detracting from the invention.

The method 200 begins at 202 with a user placing a laundry load into the treating chamber 18. With the laundry load in the treating chamber 18, the user closes the door 24 and initiates a cycle of operation of the washing machine 10 through the user interface 98. The controller 96 then determines at 204 a dry density of the laundry load, that is, the density of the laundry load with the laundry load in a dry state or condition. The dry density may be determined in any suitable manner. For example, the dry density may be determined by determining the mass of the dry laundry load and the volume of the dry laundry load and calculating the dry density by dividing the dry mass by the dry volume to obtain a dry quotient. The dry mass may be obtained by using one of the methods described above, with or without employing the load mass sensor 106, or another method not described above. Similarly, the dry volume may be obtained by using one of the methods described above, with or without employing the load volume sensor 110, or another method not described above. As an example, the dry mass may be obtained using the load mass sensor 106 in the form of load cells incorporated into the suspension system 28, while the dry volume may be determined using the load volume sensor 110 in the form of the imaging device 112.

Once the dry density has been ascertained, the controller 96 proceeds with the method 200 at 206 by wetting the laundry. The wetting of the laundry may be incorporated into a phase of the cycle of operation, such as a prewash or wash phase. The laundry load may be wet with liquid, such as water, through the liquid supply system and, optionally, the liquid may be combined with a treating aid through the dispensing system. The liquid and treating aid may be mixed prior to being supplied to the treating chamber 18 and/or mixed within the treating chamber 18 with the laundry load.

The liquid may wet the laundry load to a desired degree of saturation. For example, the laundry load may become fully saturated wherein the laundry load absorbs an amount of water at or near a maximum limit of absorption for the laundry load. In other words, the laundry load may be fully saturated or nearly fully saturated whereby any additional amount of water that the laundry load is able to absorb is negligible compared to the total amount of water that the laundry load is capable of absorbing. Alternatively, the laundry load may become partially saturated wherein the laundry load absorbs only a portion of the total amount of water that the laundry load is capable of absorbing. The degree of saturation depends, in part, on a desired resolution of the fabric type determination, which increases with increasing saturation, balanced with benefits resulting from an earlier (i.e., before achieving full saturation) determination of fabric type, such as setting water amounts and temperature and detergent dosage based on fabric type prior to supplying a large amount of water and/or detergent that may be excessive depending on the determined fabric type. Further, the degree of saturation may extend to beyond full saturation wherein the laundry load is in a dynamic free-floating state and can hold more liquid, about ten percent, than when saturated in a static state. The beyond saturation condition may also include a state where the items in the laundry load form pockets that hold water that is not actually absorbed by the fabric.

Alternatively, the liquid may be supplied to a desired liquid-to-cloth ratio (LCR), which can also be referred to as a water-to-cloth ratio (WCR) when the liquid is predominantly water. In this case, the dry mass of the laundry load may be employed to determine the amount of liquid to supply. A 5 kg dry mass for the laundry load, for example, would correspond to a supply of 5 kg of liquid to achieve a LCR of 1 and a supply of 7.5 kg of liquid for a LCR of 1.5. Any desired LCR equal to or greater than 0 and up to a maximum LCR may be used to determine the amount of supplied liquid with the understanding that different types of laundry have different maximum LCRs due to the saturation behavior of the fabrics (i.e., some fabrics can hold more liquid than others and can, therefore, reach a higher LCR). The maximum LCR may be the saturation limit for the laundry load or may correspond to a condition where the laundry load is beyond saturation in a dynamic state where the laundry load is free-floating can hold more liquid, about ten percent, than when saturated in a static state. The beyond saturation condition may also include a state where the items in the laundry load form pockets that hold water that is not actually absorbed by the fabric.

When the liquid is supplied to wet the laundry load, the liquid level in the treating chamber 18 may depend on the desired degree of saturation or LCR and the configuration of the washing machine 10. For example, when the laundry load is to be partially saturated or the LCR is relatively low, the liquid level in the treating chamber 18 may be lower than the level of the laundry load in the treating chamber 18. In some instances, the liquid level may be lower than the level of the laundry load even when the laundry load is to be fully saturated, such as if the liquid is supplied directly onto the laundry load rather than to the bottom of the tub 14.

With the laundry load wetted, the controller 96 then determines at 208 a wetted density of the laundry load, that is, the density of the laundry load with the laundry load in a wetted state or condition, which, as described above, can be partially or fully saturated. The wetted density may be determined in any suitable manner. The wetted density may be determined with the same method or a different method as used in 204 for determining the dry density. For example, the wetted density may be determined by determining the mass of the wet laundry load and the volume of the wet laundry load and calculating the wetted density by dividing the wetted mass by the wetted volume to obtain a wetted quotient. The wetted mass may be obtained by using one of the methods described above, with or without employing the load mass sensor 106, or another method not described above. Similarly, the wetted volume may be obtained by using one of the methods described above, with or without employing the load volume sensor 110, or another method not described above. As an example, the wetted mass may be obtained using the load mass sensor 106 in the form of load cells incorporated into the suspension system 28, while the wetted volume may be determined using the load volume sensor 110 in the form of the imaging device 112.

After obtaining the wetted density in the step 208, the controller 96 compares the dry density and the wetted density at 210 and determines the fabric type based on the comparison at 212. The comparison may involve any suitable type of analysis of the dry density and the wetted density to identify a difference, if any, between the dry and wetted densities. The comparison of the densities reflects a physical change in the laundry load that depends on the fabric type. Different types of fabric exhibit varying characteristics that are manifested in the difference between the dry and wetted density values, such as liquid absorbency by the fabric and collapsing of the fabric resulting from hydrogen bonding between the fabric fibers and water molecules. For example, as separate loads of synthetic fabrics and cotton fabrics having the same mass are wetted, the cotton fabrics initially collapse to a much greater degree than the synthetic fabrics due to the hydrogen bonding between the cotton fibers and the water molecules, such that the change in the density of the cotton fabrics is high relative to that of the synthetic fabrics. Within the vast variety of cotton fabrics, dry terry cloth is less dense than dry denim, but when the fabrics become wetted, the terry absorbs more liquid than denim, which results in a higher wetted density for the terry cloth compared to the denim.

Figure 4A:
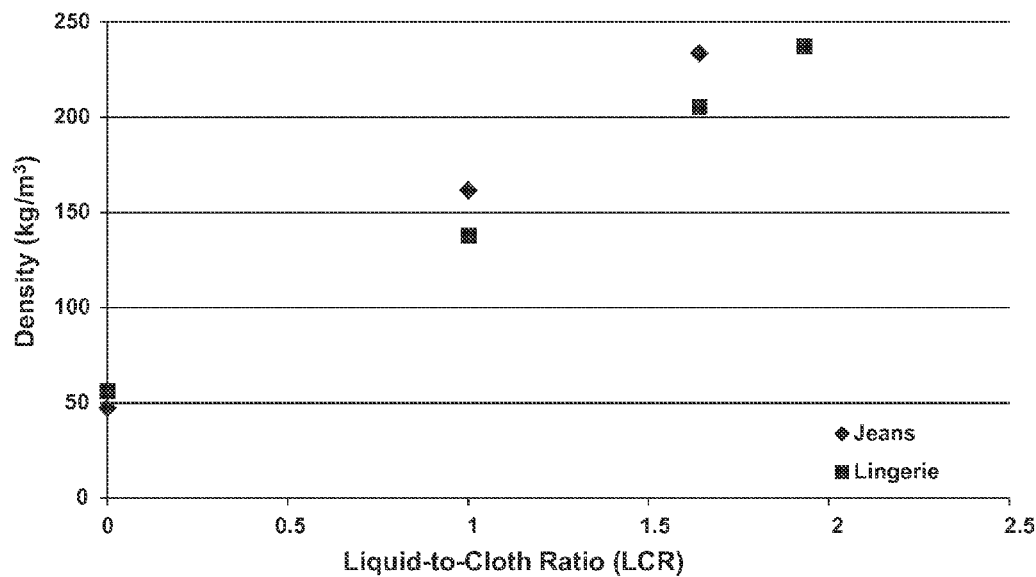
FIG. 4A is a graph showing test data for density of jeans and lingerie laundry loads at different liquid-to-cloth ratios.
Figure 4B:
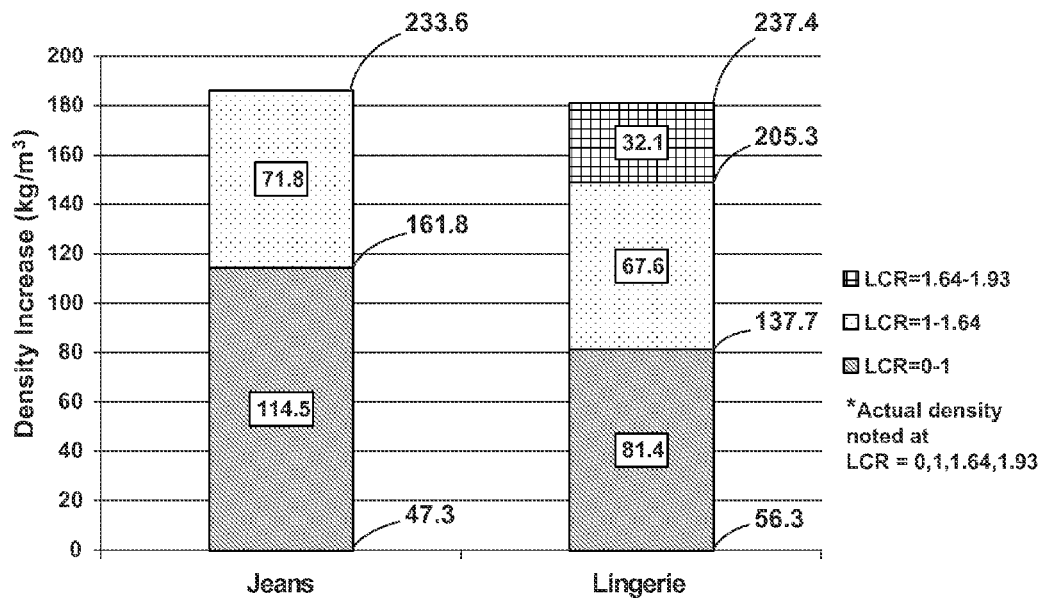
FIG. 4B is a chart showing density increases at different liquid-to-cloth ratios for the jeans and lingerie laundry load test data of FIG. 4A.

FIGS. 4A and 4B display test data for the density of 3.6 kg laundry loads of denim jeans (cotton) and lingerie (synthetic) before and during liquid supply. The density values were determined with the laundry loads in the dry condition (LCR=0) and with LCR=1, 1.64 (the saturation limit for the jeans), and 1.93 (the saturation limit for the lingerie). FIG. 4A displays the actual density values as a function of LCR, while FIG. 4B compares the incremental increases in density at each LCR with the actual density value noted next to the bar at each LCR. As seen in both graphs, the jeans undergo a relatively large volumetric collapse during the liquid supply to LCR=1 when compared to the lingerie. The jeans load exhibited a 242% density increase, while the lingerie load density increased 145%. At the saturation limit for the jeans of LCR=1.64, the jeans load showed a 394% density increase from the dry condition compared to a 265% increase for the lingerie load. The data, therefore, shows that a comparison of dry and wetted densities can be an indicator of fabric type.

In the method 200, the comparison of the dry and wetted densities may entail, as an example, determining a quantitative difference between the densities, such as by subtracting one of the densities from the other, adding the densities, or taking a ratio of the densities. When the difference is calculated by subtraction, the comparison can be a magnitude, or absolute value, of the difference. The quantified comparison can then be compared to reference values to determine the fabric type at 212. The reference values can be determined empirically, and the type of reference value may correspond to the type of quantified comparison, e.g., a subtraction difference, a sum, a ratio, etc.

The comparison may alternatively involve determining a qualitative difference between the dry and wetted densities. Ranges of quantitative densities may be categorized into desired groupings of qualitative densities, such as low, medium, and high. Each of the dry and wetted densities calculated at 204 and 208 may be compared to the ranges of densities to assign the qualitative density, such as low, medium, and high. After determination of the qualitative dry and wetted densities, the controller 96 can employ a reference, such as a look-up table, that employs the qualitative difference (i.e., the difference, if any, between the qualitative dry and wetted densities) to identify fabric types. FIG. 5 provides an exemplary table that associates at least some of the ranges for the dry density/qualitative dry density with the ranges for the wetted density/qualitative wetted density and assigns a fabric type to the associations. In the illustrative table, the synthetic fabric type has a low dry density and a low wetted density, while the bulky fabric type increases its density from low when dry to medium when wetted, and the lingerie fabric type density decreases from high when dry to low when wetted. Casual/synthetic cotton blends and denim both have a medium wetted density, but the former starts with a medium dry density with the latter having a high dry density. Finally, the terry fabric type increases its density from medium to high when wetted. The fabric types included in FIG. 5 are illustrative and are not intended to be limiting; the table may include more, fewer, and different fabric types. FIG. 6 provides another exemplary table that associates at least some of the ranges for the dry density/qualitative dry density with the ranges for the wetted density/qualitative wetted density and assigns fabric properties to the associations. In this example, rather than assigning names such as bulky, casual, etc. to the fabric type, the fabric types are described according to their properties, and the exemplary properties employed in the table are absorbency, bending, and elasticity, which are each ranked as low, medium, and high. For example, according to the table, a medium dry density and a medium wetted density corresponds to a fabric type with medium absorbency, low bending, and medium elasticity. The table may employ any suitable fabric property deemed advantageous in describing a fabric type and is not limited to those shown in the exemplary table of FIG. 6.

Regardless of the type of table, the controller 96 may compare the dry and wetted densities by identifying the row of the table corresponding to the appropriate dry density and the column of the table corresponding to the appropriate wetted density and determine the fabric type by locating the intersection of the row and column at 210 and 212. The reference table can be empirically determined and can have any suitable resolution. Employing a larger number of qualitative densities provides greater resolution of fabric type and may provide better differentiation of fabric types that are confounded at a lower resolution.

Once the fabric type has been determined, the controller 96 may set one or more parameters for the selected operation cycle based on the determined fabric type at 214 in FIG. 3. Exemplary parameters include, but are not limited to, water amount or level, water temperature, detergent dosage, duration of a wash phase or other phases of an operation cycle, soak time, drum rotation speed and rotation duration, such as during washing, rinsing, and/or spinning operations, and other motor-related signals. The operation cycle may then proceed, such as by resuming the prewash or wash phase, with the set parameters.

The method 200 of determining the fabric type of the laundry load may be executed at any phase of the operation cycle. While it is preferred to execute the method as early as possible in the operation cycle in order to set the parameters depending on the fabric type, it is feasible to determine the wetted density at any desired phase with it being understood that the dry density must be determined prior to wetting the laundry load.

The density of the laundry load, whether the dry or wetted density, may be determined by calculating the mass divided by the volume of the laundry load, and it is also well within the scope of the invention to determine the density directly, such as with inertia values. For example, the dry density may be determined by determining a first inertia value during rotation of the drum at a spin speed with the laundry load in the dry state, and the wetted density may be determined by determining a second inertia value during rotation of the drum at a spin speed with the laundry load in the wetted state. It follows that the dry and wetted density may be compared by determining a difference between the first inertia value and the second inertia value. The inertia values are indicative of the density because as the inertia determination is done while the drum is rotated at a speed sufficient to hold the laundry against the inner surface of the drum by centrifugal force, which forces the laundry to take on an annular shape whose outer periphery is limited by the inner surface of the drum. When the laundry is dry, the radial thickness of the annulus will be greater than when the laundry is wet. The variation in the radial thickness is indicative to the change in the volume between the dry and wet conditions. While some liquid remains in the laundry at these speeds, most of the liquid is removed from the laundry, which tends to minimize the effect of the additional mass of the water in the inertia determination for the wetted load. Plus, it is possible to determine an adjustment for the inertia to compensate for the liquid retained in the wetted load so that the wetted inertia reading more accurately represents the load. In these conditions, a comparison of the dry inertia and the wet inertia may be used to represent a comparison of the densities of the load under wet and dry conditions. The inertia method and other known methods of density determination may be incorporated into the method 200 of determining the fabric type.

The method 200 of determining the fabric type of the laundry load has been described as comprising a comparison of the density of the laundry load in the dry state and in a wetted state; however, fabric type may also be determined by comparing densities of laundry load in non-dry conditions. For example, the density of the laundry load may be determined after the laundry load has been partially saturated and again after the laundry load is more saturated, such as more partially saturated or fully saturated, and the two determined densities may be compared to determine the fabric type. Referring back to FIGS. 4A and 4B, as an example, comparing the density of the laundry at LCR=1 to the density of the laundry at full saturation, which would be LCR=1.64 for the jeans laundry load and LCR=1.93 for the lingerie laundry load, shows that the lingerie undergoes a larger density change than the jeans, 99.7 kg/m3 compared to 71.8 kg/m3, which amounts to 72% and 44% density changes, respectively.

Figure 7:
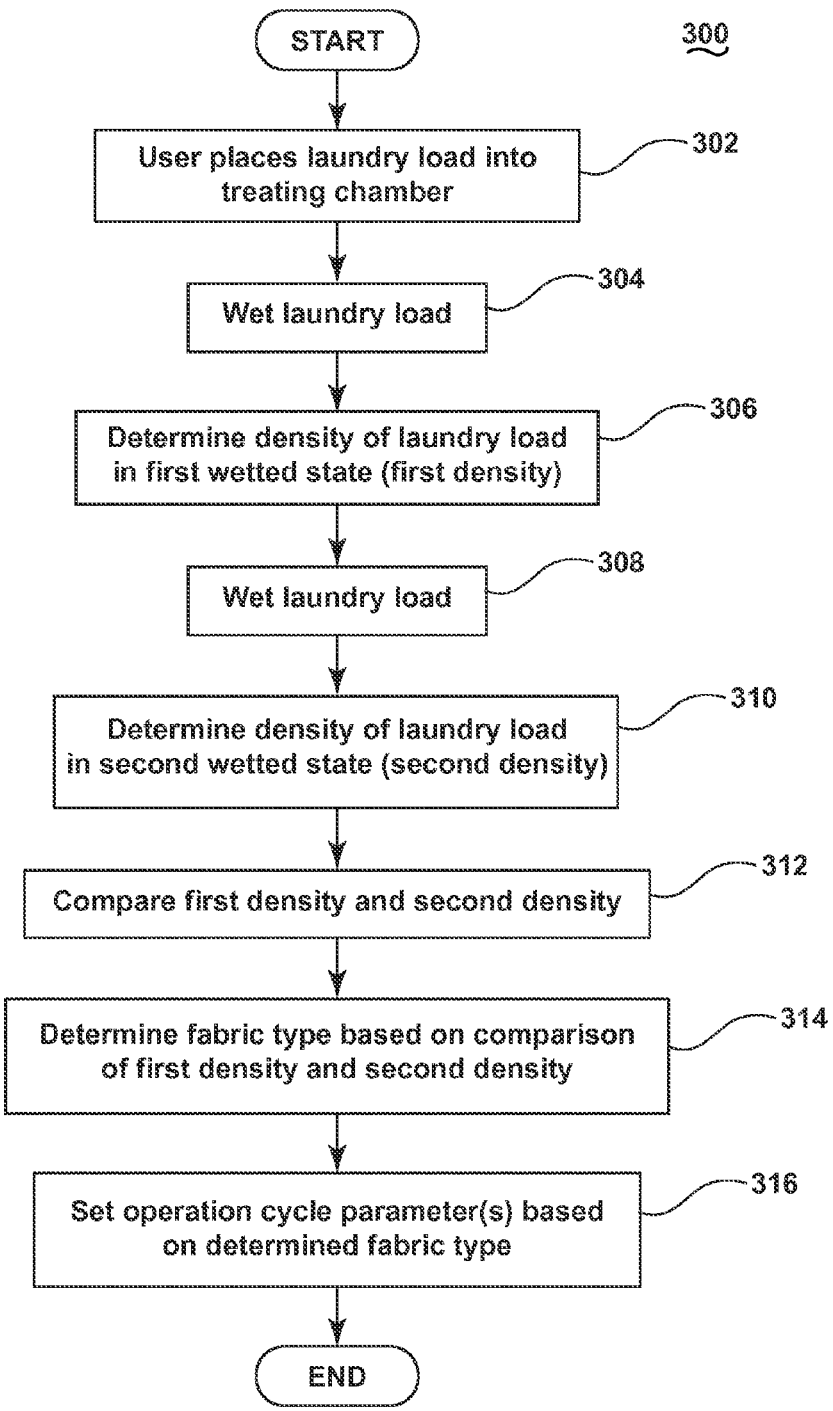
FIG. 7 is a flow chart of an embodiment of a method of determining fabric type based on densities of the laundry load in first and second wetted states.

Referring now to FIG. 7, a method 300 of determining the fabric type of the laundry load may be adapted from the method 200 in FIG. 3 by adding a wetting of the laundry load at 304 before an initial density determination at 306. The wetting of the laundry load 304 may occur in the same manner as described above for the wetting of the laundry load 206 in the method 200, including wetting the laundry load to a desired saturation level and/or to a desired LCR. The method 300 is identical in all other respects to the method 200 of FIG. 3, and the explanation provided above for the method 200 applies to the method 300, with the understanding that the dry state and the wet state of the method 200 correspond to the first wetted state and the second wetted state, respectively, of the method 300 and that the dry density and the wet density of the method 200 correspond to the first density and the second density, respectively, of the laundry load in the method 300. Thus, the invention can be considered a method of determining the fabric type of a laundry load by comparing a first density of the laundry load in a first wetted state, which can be a dry state or a partially saturated state, to a second density of the laundry load in a second wetted state, which can be a state wherein the laundry load is more wetted than in the first wetted state such that the laundry load is partially saturated, fully saturated, or beyond fully saturated.

Additionally, the methods 200, 300 may be modified to conduct density determinations, including any measurements related thereto, such as mass and volume determinations, dynamically for the laundry load rather than statically. The determinations would account for changes that may occur in the fabric as a function of time, temperature, motor speed, and other factors. For example, the volume of the fabric may change as time progresses, which may be indicative of fabric type. Such dynamic calculations may include integration and differentiation signal processing methods. As an example of how fabric may change with motor speed, certain forces may be applied to the fabric at specific speeds, and measurements of the thickness change of fabric at those speeds may assist in determining volume and, thus, density.

While the invention has been specifically described in connection with certain specific embodiments thereof, it is to be understood that this is by way of illustration and not of limitation, and the scope of the appended claims should be construed as broadly as the prior art will permit.

What is claimed is:

1. A method of determining a fabric type for a laundry load located within a treating chamber defined by a rotatable drum of a laundry treating appliance configured to treat the laundry according to an automatic cycle of operation, the method comprising:

determining a density of the laundry load in a first wetted state to define a first density;
determining a density of the laundry load in a second wetted state to define a second density;
comparing the first density and the second density; and
determining a fabric type based on the comparison.

2. The method of claim 1 wherein the comparison comprises determining a difference between the first density and the second density.

3. The method of claim 2 wherein the fabric type is a function of the magnitude of the difference.

4. The method of claim 2 wherein determining the difference comprises determining a quantitative difference.

5. The method of claim 2 wherein determining the difference comprises determining a qualitative difference.

6. The method of claim 5 wherein determining a qualitative difference comprises:

categorizing ranges for the first density and the second density;
associating at least some of the ranges for the first density with ranges for the second density; and
assigning a fabric type to at least some of the associated ranges.

7. The method of claim 6 wherein the categorized ranges for the first density comprise at least: low, medium, and high; the categorized ranges for the second density comprise at least: low, medium, and high; and at least one of the following associations is made:

low first density is associated with the low second density to represent a synthetic fabric type;
low first density is associated with the medium second density to represent a bulky fabric type;
medium first density is associated with the medium second density to represent a blend of synthetic and cotton fabric types;
medium first density is associated with the high second density to represent a terry cotton fabric type;
high first density is associated with the low medium second density to represent a lingerie fabric type; and
high first density is associated with the medium second density to represent a jeans cotton fabric type.

8. The method of claim 1 wherein determining the first density comprises determining a first inertia value during rotation of the drum at a spin speed with the laundry load in the first wetted state, determining the second density comprises determining a second inertia value during rotation of the drum at a spin speed with the laundry load in the second wetted state, and comparing the first density and the second density comprises determining a difference between the first inertia value and the second inertia value.

9. The method of claim 1 wherein determining the first density comprises determining a first volume of the laundry load in the drum while the laundry load is in the first wetted state, determining a first mass of the laundry load while the laundry load is in the first wetted state, and determining a first quotient of the first mass divided by the first volume.

10. The method of claim 9 wherein determining the second density comprises determining a second volume of the laundry load in the drum while the laundry load is in the second wetted state, determining a second mass of the laundry load while the laundry load is in the second wetted state, and determining a second quotient of the second mass divided by the second volume.

11. The method of claim 10 wherein at least one of the first volume and the second volume is determined by digitally imaging the laundry load within the treating chamber.

12. The method of claim 1 wherein the second wetted state comprises the laundry load being at least partially saturated.

13. The method of claim 12 wherein the first wetted state comprises the laundry load being dry.

14. The method of claim 12 wherein the second wetted state comprises the laundry load being fully saturated.

15. The method of claim 12 wherein the second wetted state comprises the laundry load being beyond saturation in a dynamic state.

16. The method of claim 12 wherein the first wetted state comprises the laundry load being at least partially saturated, and the second wetted state comprises the laundry load being more saturated than in the first wetted state.

17. The method of claim 1, further comprising wetting the laundry load with liquid prior to determining the second density.

18. The method of claim 17 wherein the wetting of the laundry load comprises supplying liquid to achieve a predetermined liquid-to-cloth ratio.

19. The method of claim 17 wherein wetting the laundry load comprises supplying liquid to a level in the treating chamber lower than the level of the laundry load in the treating chamber.

20. The method of claim 1, further comprising setting at least one of the following parameters for the automatic cycle of operation according to the determined fabric type: water amount, water temperature, detergent amount, drum rotation speed, wash duration, and soak time.

* * * * *